(12) United States Patent
Tham et al.

(10) Patent No.: US 7,766,857 B2
(45) Date of Patent: Aug. 3, 2010

(54) NON-INVASIVE DETERMINATION OF CARDIAC OUTPUT, GAS EXCHANGE AND ARTERIAL BLOOD GAS CONCENTRATION

(75) Inventors: Robert Q. Tham, Middleton, WI (US); Andreas Tzanetakis, Helsinki (FI)

(73) Assignee: General Electric Company, Schenectady, NY (US)

(*) Notice: Subject to any disclaimer, the term of this patent is extended or adjusted under 35 U.S.C. 154(b) by 1017 days.

(21) Appl. No.: 11/465,913

(22) Filed: Aug. 21, 2006

(65) Prior Publication Data
US 2008/0041381 A1 Feb. 21, 2008

(51) Int. Cl.
- A61M 37/00 (2006.01)
- A61N 1/30 (2006.01)
- A61M 31/00 (2006.01)
- A61M 16/00 (2006.01)

(52) U.S. Cl. ............ 604/23; 604/19; 604/93.01; 128/204.18

(58) Field of Classification Search ........... 128/204.18, 128/205.11–205.12; 604/23–28, 30, 503, 604/507–508, 93.01; 600/301, 364, 529, 600/532
See application file for complete search history.

(56) References Cited

U.S. PATENT DOCUMENTS

| | | | |
|---|---|---|---|
| 3,927,981 A * | 12/1975 | Viannay et al. | 422/48 |
| 4,516,580 A | 5/1985 | Polanyi | |
| 4,911,689 A | 3/1990 | Hattler | |
| 5,207,640 A | 5/1993 | Hattler | |
| 5,336,164 A | 8/1994 | Snider et al. | |
| 5,487,727 A * | 1/1996 | Snider et al. | 604/508 |
| 5,501,663 A | 3/1996 | Hattler et al. | |
| 5,743,259 A * | 4/1998 | Kruse et al. | 600/309 |
| 5,865,789 A | 2/1999 | Hattler | |
| 5,954,050 A * | 9/1999 | Christopher | 128/204.23 |
| 6,238,365 B1 * | 5/2001 | Gord et al. | 604/26 |
| 6,629,934 B2 * | 10/2003 | Mault et al. | 600/538 |
| 6,659,961 B2 * | 12/2003 | Robinson | 600/531 |
| 6,702,783 B1 * | 3/2004 | Dae et al. | 604/113 |
| 2004/0059239 A1 * | 3/2004 | Jaffe et al. | 600/529 |
| 2004/0228930 A1 * | 11/2004 | Billiar et al. | 424/699 |
| 2005/0133032 A1 * | 6/2005 | Berthon-Jones et al. | 128/204.23 |
| 2006/0129087 A1 * | 6/2006 | Uesugi et al. | 604/26 |
| 2007/0129666 A1 * | 6/2007 | Barton et al. | 604/26 |

* cited by examiner

Primary Examiner—Justine R Yu
Assistant Examiner—Rachel T Young
(74) Attorney, Agent, or Firm—Andrus, Sceales, Starke & Sawall, LLP

(57) ABSTRACT

A system and method for monitoring the arterial gas concentrations of a patient receiving percutaneous oxygenator support. The system comprises a percutaneous oxygenator for providing medical gases to the venous system of the patient via a catheter. Gases are also removed from the venous system via a catheter. The concentrations and flow rates of the gases provided and removed from the patient are monitored. A CPU analyzes the concentration and flow rate information to compute the arterial gas concentration of the patient.

19 Claims, 1 Drawing Sheet

NON-INVASIVE DETERMINATION OF CARDIAC OUTPUT, GAS EXCHANGE AND ARTERIAL BLOOD GAS CONCENTRATION

FIELD OF THE INVENTION

The present invention is directed to the field of blood gas monitoring, specifically the non-invasive monitoring of arterial blood gas concentration.

BACKGROUND OF THE INVENTION

Percutaneous oxygenators have been described in the prior art for more than twenty years. As disclosed in U.S. Pat. No. 4,911,689 to Hattler, a percutaneous oxygenator comprises a number of hollow, gas-permeable fibers. This device is inserted through a single small incision into a patient's venous system. When an oxygen supply is attached to the device, oxygen flows through the hollow fibers and diffuses through the wall of the fibers into the patient's blood. Conversely, carbon dioxide from the blood diffuses back across the fiber wall, up the fibers and out of the system to the atmosphere. While improvements to this design have been made, to date, no percutaneous oxygenator is able to fully provide the necessary oxygenation required. At best performance, prior art oxygenators may supply 50%-70% of required metabolic oxygen. Therefore, it has been proposed that percutaneous oxygenators may be used to augment natural patient respiration or mechanical ventilation support already provided to the patient through the patient's airway. The augmentation of the natural patient respiration may allow a patient to avoid mechanical ventilation. For a patient who is already receiving mechanical ventilation support, the introduction of percutaneous oxygenator support would reduce the demand for aggressive ventilatory treatment. This is desirable due to the fact that aggressive ventilatory treatment may cause lung injury or increase the cardiac stresses on the patient.

Percutaneous oxygenator technology is not limited in scope to merely the delivery of supplemental oxygen. The same catheterization technique of the patient with gas-permeable membrane fibers can be used to deliver a variety of medical gases intravenously into the patient's blood stream. This technique may be used to deliver anesthetic agent, or other medical gases such as carbon dioxide ($CO_2$), nitrogen (N), nitrous oxide (NO), or helium (He).

Typically, when a patient is receiving ventilatory support, the effectiveness of this support is monitored using a spirometer and respiratory gas monitor such as the Datex-Ohmeda S5 Gas Analyzer. The data collected from the spirometer and gas monitor is used to monitor the composition, flow rates, and exchange rates of the gases inspired and expired by the patient. However, patients receiving mechanical ventilatory support often have compromised gas exchange in their lungs. A patient receiving supplemental percutaneous oxygenator support often results in the erroneous prediction or estimation of the patient's blood gas concentration due to mismatched blood-gas exchange and compromised gas diffusion across the alveoli. Solutions to this problem have been invasive and time-consuming. Typically, blood samples must be drawn intermittently and individually analyzed to assess the patient's actual blood gas concentration and evaluate the adequacy of the combined treatment. While systems have been developed to automatically sample and analyze the patient's blood gas concentration, such as that disclosed in U.S. Pat. No. 4,516,580 to Polanyi, these systems require the invasive arterial insertion of a costly multi-parameter, multi-sensor transducer.

Despite improvements, all of the aforementioned systems are limited in their ability to continuously monitor a patient's blood gas concentration. All of these systems and methods require the taking of an actual blood sample. This inherently reduces the sampling rate of the patient's blood and additional time is required to compute the blood gas concentration. These delays produce a lag time that can inaccurately display the patient's blood gas concentration.

It is therefore desirable for a system by which the blood gas concentration of a patient receiving both mechanical ventilation and percutaneous oxygenator support may be determined without the introduction of an invasive intravascular transducer. It is also desirable for a system by which components already used in conjunction with or associated with the mechanical ventilation and/or percutaneous oxygenation of a patient are used to determine patient blood gas concentration.

SUMMARY OF THE INVENTION

An embodiment of the present invention is a system that comprises exchange catheter gas composition data, such as the composition and flow rates in and out of a percutaneous oxygenator to determine patient venous blood gas concentration resulting in continuous computation of patient arterial blood gas concentration.

In a further embodiment of the present invention, the exchange catheter gas composition data combines with pre-existing gas analysis data from the mechanical ventilation system comprising gas analyzer and spirometry data to continuously compute cardiac output trending, blood gas exchange analysis, and arterial gas concentrations.

It is a further aspect of the present invention that the present invention provides a continuous and noninvasive solution to the computation of arterial blood gas concentration.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
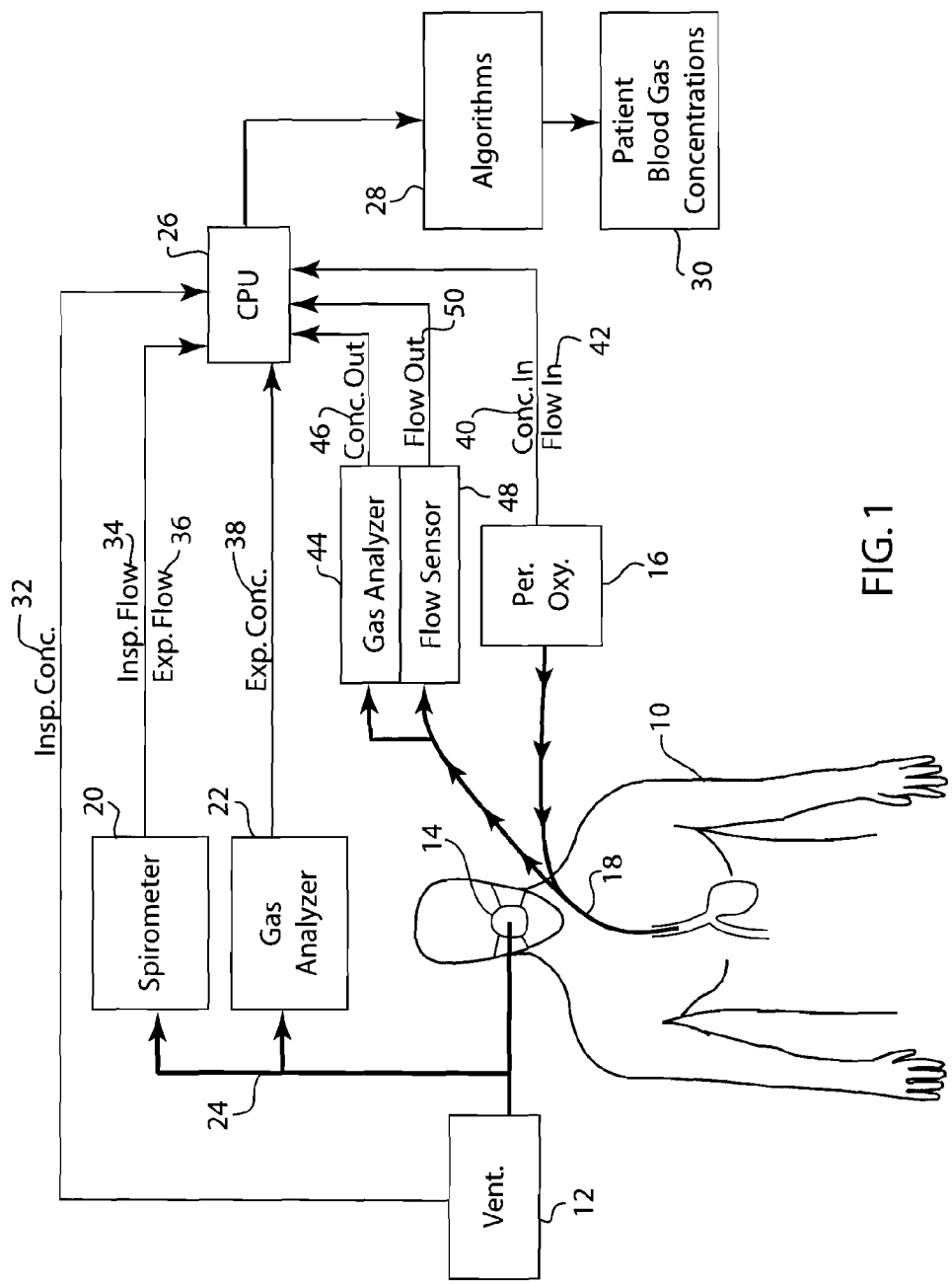
FIG. 1 is a schematic diagram of the patient analysis system of the present invention.

FIG. 1 depicts a schematic diagram of a patient receiving both mechanical ventilation as well as percutaneous oxygenator support. The patient 10 receives mechanical ventilation support from a ventilator 12 via a patient interface 14 such as a face mask or endotracheal tube. The patient's mechanical ventilation support is augmented by a percutaneous oxygenator 16 which introduces an additional supply of oxygen to the patient venous blood via a gas exchange catheter 18 which is inserted into the patient's superior or inferior vena cava.

In a typical clinical setting where a patient is undergoing mechanical ventilation support the ventilator 12 is used in conjunction with a spirometer 20 and a gas analyzer 22 which receive samples of the gas inspired and expired by the patient 10 via a gas sampling tube 24. Alternatively, mainstream gas analyzers that measure gas concentration directly from the patient gas stream without having the gases sampled via a tube may also be used. The spirometer 20 monitors the volume and flow rate of the air that is inspired and expired by the patient. The gas analyzer 22 derives the concentrations of the different component gases breathed by the patient 10.

Referring back to the present invention as depicted in FIG. 1, a CPU 26 collects data from a variety of sources including the ventilator 12, percutaneous oxygenator 16, the spirometer 20, and the gas analyzer 22. Then the CPU processes this data through a series of algorithms 28 by which the patient's blood gas concentration 30 is derived.

The present invention will be described in consideration of the exchange of oxygen to the venous blood stream and the related computation of the oxygen exchange and arterial oxygen concentration. However, it is understood that a similar device arrangement and method can be used to compute other gas exchanges and arterial concentrations, such as carbon dioxide ($CO_2$), nitrogen (N), nitrous oxide (NO), helium (He), carbon monoxide (CO), or anesthetic gases. As previously stated, the CPU 26 receives data relating to the patient's blood gas concentration from a variety of sources connected to the patient. As the ventilator provides inspiratory support to the patient 14, the concentration of inspired oxygen 32 is provided to CPU 26. The spirometer 20 provides data to the CPU 26 representing the inspiratory flow rate 34 and the expiratory flow rate 36. The gas analyzer 22 provides CPU 26 with data representative of the concentration of expired oxygen 38 of the patient 10.

As additional oxygen support is provided to the patient by the percutaneous oxygenator 16, the individual flow rates of the component gases entering the catheter 18 are known either by the manual control settings of the gases by the clinician or by the measurement of the gas concentration and flow rate by a separate component downstream (not pictured). The gas concentration and flow rate data, namely the concentration of oxygen going into the catheter 40 and the flow rate of oxygen into the catheter 42 are sent to CPU 26. As gases exit the distal end of the catheter 18, the concentration of the component gases are determined by a second gas analyzer 44 that provides data representative of the concentration of oxygen 46 coming out of the catheter 18 to CPU 26. The total flow of the gases out of the catheter 18 is measured by a flow sensor 48 and is provided to the CPU 26 as the total flow out of the catheter 50.

The CPU 26 uses the data that it has received, as described above, with a variety of algorithms to be herein described further. By using the law of conservation of mass, the gas exchange and arterial oxygen concentration can be computed as herein described. Included Table I is a summary of the variables used in the following equations, a description of the variable, the source of this value, and an associated reference number if applicable.

TABLE I

| Variables | Description | Source | Ref. # |
|---|---|---|---|
| $V_h$ | Effective gas exchange volume of the intravenous gas exchange catheter | Calculated (Eq. 1) | — |
| $C_{O2out}$ | Concentration of O2 out of the catheter | Gas Analyzer (44) | 46 |
| $F_{O2in}$ | Flow of O2 into the catheter | P.O. (16) | 42 |
| $F_{tot\_out}$ | Total Flow out of the catheter | Flow Sensor (48) | 50 |
| $K_{eff}$ | Gas equilibration coefficient | Constant/Known | — |
| $C_{venousO2}$ | Concentration of venous O2 | Calculated (Eq. 2) | — |
| CO | Average Cardiac Output | Calculated (Eq. 3) | — |
| $C_{artO2}$ | Average Concentration of arterial O2 | Calculated (Eq. 7) | 30 |
| $C_{inspO2}$ | Concentration of inspired O2 | Ventilator (12) | 32 |
| $F_{insp}$ | Flow of inspired gases | Spirometer (20) | 34 |
| $C_{expO2}$ | Concentration of expired O2 | Gas Analyzer (22) | 38 |
| $C_{O2in}$ | Concentration of O2 into the catheter | P.O. (16) | 40 |
| $C_{returnO2}$ | Concentration of venous return O2 | Calculated (Eq. 6) | — |
| $F_{exp}$ | Flow of expired gases | Spirometer (20) | 36 |

By definition, the mixed venous concentration of oxygen entering the right atria can be computed using the gas equilibration coefficient, $K_{eff}$, which is known to the system by the design or calibration of the percutaneous oxygenator 16, $$V_h * \frac{d(C_{O_2 out})}{dt} = F_{O_2 in} - [C_{O_2 out} * F_{tot\_out}] - K_{eff} * [C_{O_2 out} - C_{(venousO)_2}] \quad (\text{Eq. 1})$$

At steady state and in the catheter flow condition labeled as __1, the derivative of $C_{O2out\_1}$ with respect to time, tends to zero, giving the steady state concentration of the venous blood to the right atria to be:

$$C_{venousO_2\_1} = (C_{O_2out\_1} - F_{tot\_out}) - F_{O_2in\_1} + K_{eff} * C_{O_2out} \quad (\text{Eq. 2})$$

Now considering the gas exchange in the lungs, by integrating over a breath, the arterial oxygen concentration can be found by solving the following integral equation:

$$\int (CO * C_{artO_2}) dt = \int (CO * C_{venousO_2\_1} + C_{inspO_2} * F_{insp} - C_{expO_2} * F_{exp}) dt \quad (\text{Eq. 3})$$

Where CO is the cardiac output and can be found by using two different settings of $C_{O2in}$ 42 or $F_{O2in}$ 40.

Now assuming that the concentration of O2 in the catheter is being altered from a condition__1 to condition__2, and set in a duration that is much shorter than the recirculation time of blood, but is sufficiently long for a steady state to settle, the uptake of O2 surrounding the compartment around the catheter 18 and the vena cava at a steady state in the two conditions are described by the two gas mass balance equations, $$\int (F_{O_2in\_1} - (C_{O_2\_out\_1} * F_{tot\_out\_1})) dt = \int (CO * (C_{returnO_2} - C_{venousO_2\_1})) dt \quad (\text{Eq. 4})$$

$$\int (F_{O_2in\_2} - (C_{O_2\_out\_2} * F_{tot\_out\_2})) dt = \int (CO * (C_{returnO_2} - C_{venousO_2\_2})) dt \quad (\text{Eq. 5})$$

Where the indices __1 and __2 indicate the settings or measurements under condition__1 and condition__2, respectively, of the oxygen concentration into the catheter 18. $C_{returnO2}$ is the flow averaged concentration of mixed venous blood in the superior or inferior vena cava and remains constant during the two settings of O2 concentration into the catheter. Furthermore, assuming that the gas flow and concentration into the catheter 18, $C_{returnO2}$ and cardiac output (CO) are constant over the two integral period, the integral expression may be removed from the integration and multiplied by the duration and can be divided out from both sides of the equations.

By subtracting the equation in condition_1 from the equation in condition_2, the unknown variable $C_{returnO2}$ is eliminated and after rearranging the resulting equation, the cardiac output is obtained:

$$CO = \frac{((F_{O_2in\_1} - (C_{O_2out\_1} * F_{tot\_out\_1})) - ((F_{O_2in\_2} - (C_{O_2out\_2} * F_{tot\_out\_2})))}{(C_{venousO_2\_2} - C_{venousO_2\_1})} \quad \text{(Eq. 6)}$$

By substituting the cardiac output calculated in Equation 6 back into the arterial blood gas equation, with $C_{venousO2}$ computed from Equation 2, solving Equation 3 yields the concentration of arterial oxygen 30, as shown in Equation 7.

$$C_{artO_2} = \frac{\int (CO * C_{venousO_2\_1} + C_{inspO_2} * \frac{F_{insp} - C_{expO_2} * F_{exp}}{}) dt}{\int (CO) dt} \quad \text{(Eq. 7)}$$

The arterial concentration of CO2, $C_{artCO2}$, can be derived by perturbing the inflow of gases, $F_{O2in}$, and solving a set of similarly derived equations except for the substitution of CO2 concentrations, such as $C_{CO2out}$ and $C_{venousCO2}$, for the corresponding O2 concentrations.

In an embodiment of the present invention, the CPU 26 further uses the derived patient blood gas concentrations 30 to control the operation of the percutaneous oxygenator 16 or the ventilator 12. For example, if the patient's blood gas concentration of oxygen becomes too low, the CPU may automatically adjust the oxygen concentration or the flow rate of oxygen supplied to the patient 10 by the percutaneous oxygenator 16. It is also understood that the operational controls of the ventilator 12 may be adjusted to raise the oxygen concentration in the patient's blood. The CPU 26 may adjust the respiratory rate, respiratory pressure, positive end expiratory pressure (PEEP), or the concentration of supplemental oxygen supplied by the ventilator 12. It is under stood that this automated control may be used in the control of other gases supplied to the patient as herein described. Furthermore, it is understood that in an embodiment of the present invention, CPU 26 may signal or alarm a clinician to initiate changes in the operational parameters of the percutaneous oxygenator 16 or ventilator 12 instead of automatedly performing these functions.

The advantage of this invention is that the oxygen and carbon dioxide gas exchange, and the arterial concentrations of oxygen and carbon dioxide can be computed continuously and trended without an additional arterial blood gas monitor. This reduces the cost of assessing the progression of a gas exchange therapy and replaces the time consuming and slow responding laboratory blood gas sample analysis. Therefore, the present invention provides an accurate, non-invasive approach to continuously monitoring arterial oxygenation levels of a patient receiving both mechanical ventilatory support and percutaneous oxygenation support.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

We claim:

1. A system for monitoring arterial gas concentrations of a patient receiving both mechanical ventilation support and percutaneous oxygenation support, the system comprising:
   a ventilator for providing mechanical ventilation support to a patient;
   a first flow sensor associated with the ventilator for determining a gas flow provided to the patient by the ventilator;
   a first gas analyzer associated with the ventilator for determining a gas concentration provided to the patient by the ventilator;
   a percutaneous oxygenator for providing medical gases to a venous system of the patient via a catheter, wherein the catheter also removes gases from the venous system of the patient;
   a second flow sensor associated with the gases removed from the patient via the catheter for determining a gas flow out of the catheter;
   a second gas analyzer associated with the gases removed from the patient via the catheter for determining gas concentrations associated with the gas removed from the patient via the catheter; and
   a CPU comprising an algorithm that computes a blood gas concentration of the patient;
   wherein data from the ventilator, percutaneous oxygenator, first and second flow sensors, and first and second gas analyzers is provided to the CPU and the CPU applies the data to algorithms to compute arterial gas concentrations of the patient.

2. The system for monitoring the arterial gas concentrations of a patient of claim 1 wherein the first flow sensor is a spirometer.

3. The system for monitoring the arterial gas concentrations of a patient of claim 1 wherein the system operates continuously.

4. The system for monitoring the arterial gas concentrations of a patient of claim 2 wherein the system further computes trending information with respect to the arterial gas concentrations of the patient.

5. The system for monitoring the arterial gas concentrations of a patient of claim 1 further comprising a third flow sensor associated with the medical gases provided to the patient via the catheter for determining the gas flow into the catheter, wherein data representative of the gas flow is provided to the CPU.

6. The system for monitoring the arterial gas concentrations of a patient of claim 5 further comprising a third gas analyzer associated with the medical gases provided to the patient via the catheter for determining the concentration of the medical gases provided to the patient via the catheter, wherein data representative of the concentrations of the medical gases that are provided to the patient is provided to the CPU.

7. A system for non-invasively monitoring an arterial gas concentration of a patient receiving percutaneous oxygenator support, the system comprising:

a percutaneous oxygenator for providing medical gases to a venous system of a patient via a percutaneous gas exchange catheter, wherein the gas exchange catheter also removes gases from the venous system of the patient;

a first flow sensor associated with the gas exchange catheter and determining a flow rate of the medical gases into the patient through the gas exchange catheter;

a first gas analyzer associated with the gas exchange catheter and determining a concentration of the medical gases provided to the patient through the gas exchange catheter;

a second flow sensor associated with the gas exchange catheter and determining a flow rate of the gases out of the venous system of the patient through the gas exchange catheter;

a second gas analyzer associated with the gas exchange catheter and determining a concentration of the gases removed from the patient through the gas exchange catheter; and a CPU that receives the determined flow rates and concentrations and analyzes the flow rates and concentrations to compute a arterial gas concentration of the patient.

8. The system for monitoring the arterial gas concentration of a patient of claim 7 further comprising:

a ventilator that provides respiratory gas to the patient and removes expired gas from the patient;

a spirometer connected to the ventilator that measures the flow of respiratory gas provided to the patient and the flow of expired gas from the patient; and a gas analyzer that measures the concentration of the expired gas from the patient.

9. The system for monitoring the arterial gas concentration of a patient of claim 8 wherein the spirometer provides the measured respiratory gas flow and expired gas flow to the CPU, and the gas analyzer provides the measured expired gas concentration to the CPU, the CPU computes the gas exchange in the lungs and combines the gas exchange in the lungs with the venous gas exchange to compute the arterial gas concentration of the patient.

10. The system of claim 9, wherein the computed arterial gas concentration is used to determine optimal flow and concentration settings for the percutaneous oxygenator.

11. The system of claim 9, wherein the computed arterial gas concentration is used to determine optimal operation parameters of the ventilator.

12. A method of monitoring an arterial gas concentration of a patient using a CPU comprising algorithms for executing the claimed computations, the method comprising the steps of:

providing medical gas into a blood stream of a patient with a percutaneous oxygenation catheter;

sensing a concentration and flow rate information of medical gas provided to the patient with the percutaneous oxygenation catheter;

sending the provided medical gas concentration and flow rate information to a CPU;

removing gas from the blood stream of the patient with the percutaneous oxygenation catheter;

sensing the concentration and flow rate information of gas removed from the patient with the percutaneous oxygenation catheter;

sending the removed gas concentration and flow rate information to the CPU; and computing a arterial gas concentration of the patient with the CPU;

wherein the CPU computes the arterial gas concentration from the provided medical gas concentration and flow rate information and the removed gas concentration and flow rate information.

13. The method of claim 12 further comprising:

providing mechanical respiratory support to the patient with a ventilator; and obtaining ventilatory gas exchange data comprising a flow rate and a concentration of medical gas provided to the patient by the ventilator, and a flow rate and a concentration of gas expired by the patient.

14. The method of claim 13 further comprising the steps of:

providing the ventilatory gas exchange data to the CPU; and computing the arterial gas concentration of the patient with the CPU using the ventilatory gas exchange data; in addition to the provided medical gas concentration and flow rate information and the removed gas concentration and flow rate information.

15. The method of claim 12 wherein the step of sensing the concentration and flow rate information of medical gas provided to the patient with the percutaneous oxygenation catheter is provided by the concentration and flow rate settings of a percutaneous oxygenator connected to the percutaneous oxygenation catheter.

16. The method of claim 12 wherein the percutaneous oxygenation catheter is disposed in the venous system of the patient.

17. The method of claim 16 wherein the step of sensing the concentration and flow rate information of gas provided to the patient with the percutaneous oxygenation catheter is provided by sensors disposed outside of the patient's body and coupled to the percutaneous oxygen catheter.

18. The method of claim 16 wherein the step of sensing the concentration and flow rate information of gas removed from the patient with the percutaneous oxygenation catheter is provided by sensors disposed outside of the patient's body and coupled to the percutaneous oxygenation catheter.

19. The method of claim 12 further comprising the step of computing the cardiac output of the patient from the information sent to the CPU.

* * * * *